(12) United States Patent
Robertson

(10) Patent No.: US 6,758,960 B1
(45) Date of Patent: Jul. 6, 2004

(54) ELECTRODE ASSEMBLY AND METHOD OF USING THE SAME

(75) Inventor: Peter M. Robertson, Winkel (CH)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 10/325,379

(22) Filed: Dec. 20, 2002

(51) Int. Cl.[7] .......................................... G01N 27/403
(52) U.S. Cl. ..................... 205/775; 204/402; 204/400
(58) Field of Search ................. 204/400, 402; 205/775

(56) References Cited

U.S. PATENT DOCUMENTS

| | | | | |
|---|---|---|---|---|
| 2,898,282 | A | * | 8/1959 | Flook et al. |
| 4,568,445 | A | * | 2/1986 | Cates et al. |
| 4,772,375 | A | * | 9/1988 | Wullschleger et al. |
| 5,162,077 | A | * | 11/1992 | Bryan et al. |
| 5,288,387 | A | * | 2/1994 | Ito et al. |
| 5,316,649 | A | * | 5/1994 | Kronberg |
| 6,478,950 | B1 | * | 11/2002 | Peat et al. |
| 6,558,519 | B1 | * | 5/2003 | Dodgson et al. |

* cited by examiner

*Primary Examiner*—Alex Noguerola
(74) *Attorney, Agent, or Firm*—Margaret Chappuis; Steven J. Hultquist

(57) ABSTRACT

The present invention relates to an electrode assembly that is capable of both solution measurement and in-line self-cleaning. Specifically, such electrode assembly comprises a central electrode and a measurement circuit for solution measurement, and an auxiliary electrode and an auxiliary current sourse for generating gas during intervals between solution measurement cycles, so as to remove any solid or liquid residues that may passivate the central electrode, thereby cleaning and rejuvenating the central electrode and preparing it for the next solution measurement cycle.

20 Claims, 3 Drawing Sheets

ELECTRODE ASSEMBLY AND METHOD OF USING THE SAME

BACKGROUND OF THE INVENTION

1. Field of Invention

The present invention relates to an electrode assembly that performs the dual functions of solution measurements and after-measurement self-cleaning.

2. Related Art

Many solution analytical processes use metal electrodes for collecting important analytical signals, such as current density, electropotential, and pH value, from sample solutions for determining the specific types and concentrations of components in such sample solutions.

For example, a potentiometric titration of a reduction-oxidation species in a sample solution relies on measuring a characteristic oxidation-reduction-potential (ORP) of such sample solution that is indicative of a titration endpoint, by using an ORP electrode comprising platinum or platinum alloys.

However, extended use of the metal electrode will render such electrode passivated (i.e., delayed and reduced response to changes in the sample solution) after repeated signal collection cycles, due to formation of solid or liquid residues on a surface of such electrode in contact with the sample solution. This is especially true in cases where an indicator electrode is used in precipitation titration analysis (e.g., titrations with silver nitrate).

Conventional methods for cleaning or reactivating the passivated electrode require disassembling and reassembling of the analytical cell that contains such electrode, which results in long off-time and is both time and labor consuming. Moreover, incorrect reassembling of the analytical cell may lead to subsequent system failure.

It is therefore an object of the present invention to provide a faster and easier method for rejuvenating the passivated electrode.

Other objects and advantages will be more fully apparent form the ensuing disclosure and appended claims.

SUMMARY OF THE INVENTION

The present invention provides an electrode assembly, which is capable of automated, in-line self-cleaning, without having to disassemble and reassemble the whole analytical cell, and therefore solving the above-described problems associated with conventional electrode cleaning methods.

The present invention in a specific aspect relates to an electrode assembly for collecting analytical signals from a sample solution, comprising:

(a) a central electrode;
(b) a measurement circuit;
(c) an auxiliary electrode; and
(d) an auxiliary current source,
wherein the central electrode is detachably connected to the measurement circuit during a measurement period, for collecting analytical signals from the sample solution, and wherein the central and auxiliary electrodes are detachably connected to the auxiliary current source during a cleaning period, to generate gas for in-line cleaning of such electrode assembly.

The central and auxiliary electrodes preferably comprise metal or metal alloys, such as platinum, stainless steel, copper, aluminum, gold, silver, etc., and alloys thereof. However, such central and auxiliary electrodes are not limited thereby in any manner, and they can also comprise carbon, glass, ceramic, and any other metal and/or non-metal materials suitable for manufacturing electrodes, depending on the specific uses they are intended for. For example, when the electrodes are used for measuring oxidation-reduction-potential in a sample solution, together with a suitable reference electrode, or when the electrodes are used for measuring in an amperometric technique where they are polarized by applying an electric potential or current in a sample solution, such electrodes preferably comprise platinum or platinum alloys.

In order to maximize the electrolytic gas generation, such central and auxiliary electrodes are immersed in a conductive electrolytic solution, preferably an acid solution, and the auxiliary current source passes electrical current between the central and auxiliary electrodes through the conductive electrolytic solution, to generate gas bubbles in a manner that is sufficient to peel away any solid or liquid residues or deposits on the central electrode and to reactively clean such central electrode.

Another aspect of the present invention relates to a method for rejuvenating a passivated measurement electrode, by using an electrode assembly described hereinabove.

Additional aspects, features and embodiments of the invention will be more fully apparent from the ensuing disclosure and appended claims.

DETAILED DESCRIPTION OF THE INVENTION, AND PREFERRED EMBODIMENTS THEREOF

The use of the electrode assembly of the present invention solves the electrode passivation problem commonly seen in systems using other types of electrodes. Such electrode assembly is not only capable of solution measurement, but also automatic in-line cleaning of the passivated electrode and the analytical cell in which it is disposed, via an electrolytic process in a conducting electrolytic solution.

Figure 1A:
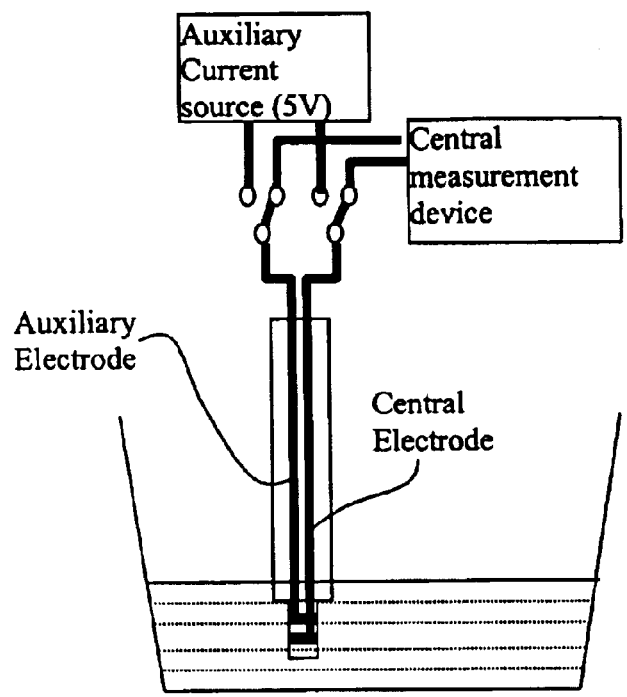
FIGS. 1A and 1B show dual platinum electrodes for following the course of an ORP titration by measuring the cell potential under polarized conditions in a sample solution, according to one embodiment of the present application.
Figure 1B:
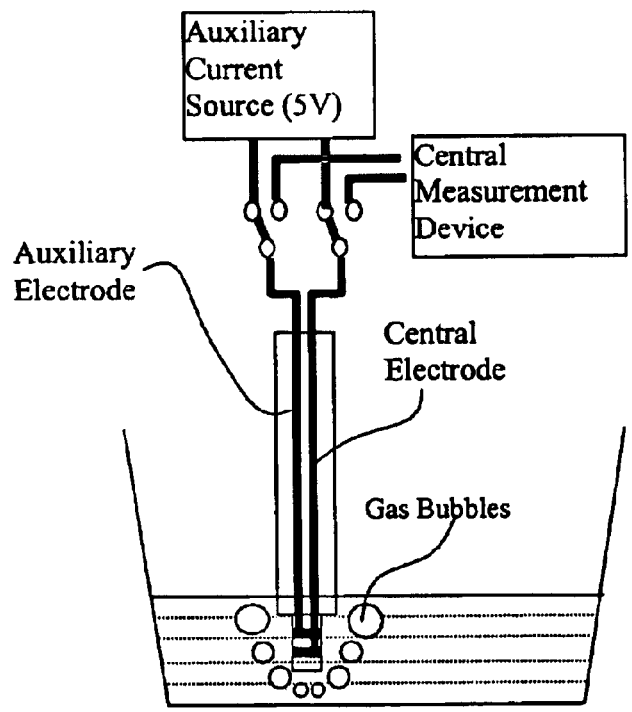

Specifically, an electrode assembly as shown in FIGS. 1A and 1B hereof can be used, which includes a central platinum electrode and an auxiliary electrode that can be connected to a measurement device and functions as the dual polarized indicator electrode pair and an auxiliary current source used solely for electrolytic gas generation.

During a solution measurement cycle, the two electrodes are detachably connected to the central measurement device for cell potential measurements of the sample solution, as shown in FIG. 1A.

Specifically, an electrode assembly as show in FIG. 3 of the present application can be used, which includes a central platinum electrode that can be connected to a measurement device and functions as the oxidation-reduction potential (ORP) electrode or it can be connected to the current source, an auxiliary electrode and an auxiliary current source used solely for electrolytic gas generation, and a reference electrode.

After the solution measurement cycle, the central electrode may become passivated due to solid or liquid residues formed thereon. Therefore, a cleaning cycle starts, in which the two electrodes are disconnected or detached from the central measurement device, and both are subsequently connected to the auxiliary current source (with an operating voltage of about 5–12 VAC) in a detachable manner, as shown in FIG. 1B. Electrical current passes through the two electrodes, generating gas bubbles and providing a vigorous surface process, which peels away any solid or liquid residues on the electrode surface that may passivate the electrode's response to the electropotential changes in the sample solution.

Therefore, the two electrodes are cleaned and reactivated, and are ready to be reconnected to the central measurement device for the next solution measurement cycle.

Figure 2:
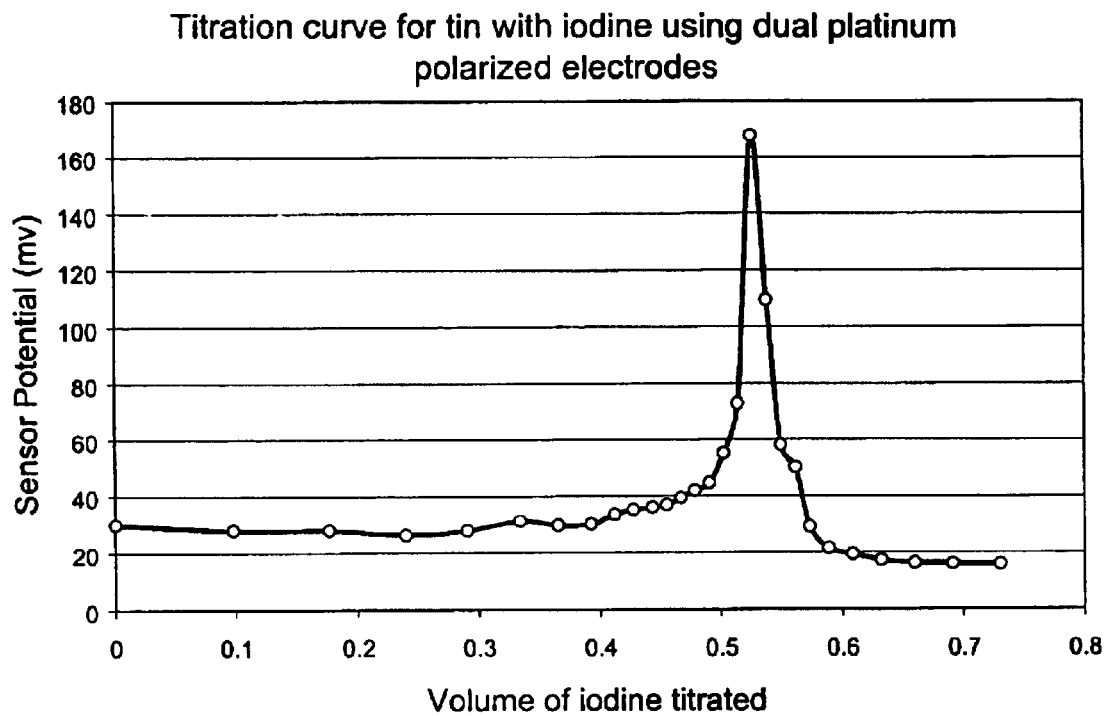
FIG. 2 is a titration curve for iodine titration of tin ions, using dual platinum polarized electrodes.

FIG. 2 shows a titration curve measured for iodine titration of tin ions in a sample solder plating solution, using an electrode assembly having platinum central and auxiliary electrodes, as described hereinabove. The measured cell potential response shows a readily determinable titration endpoint.

Figure 3A:
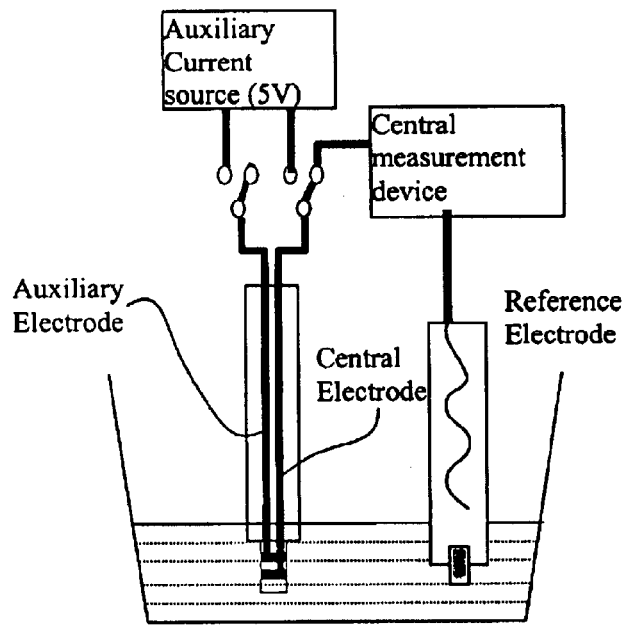
FIGS. 3A and 3B show dual platinum electrodes plus a reference electrode for measuring the ORP of a sample solution, according to one embodiment of the present application.
Figure 3B:
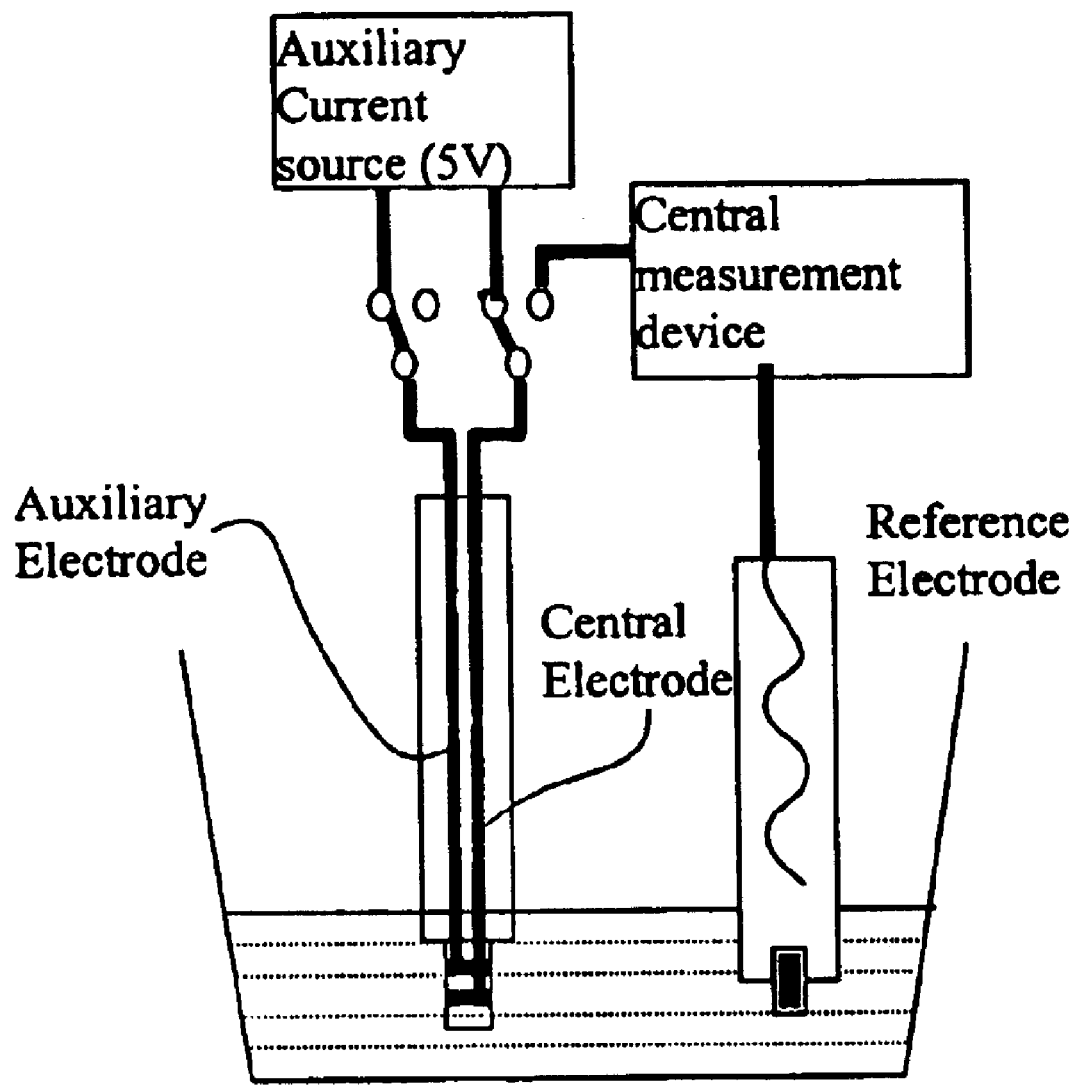

Specifically, an electrode assembly as show in FIGS. 3A and 3B of the present application can be used, which includes a central platinum electrode that can be connected to a measurement device and functions as the oxidation-reduction potential (ORP) electrode, an auxiliary electrode and an auxiliary current source used solely for electrolytic gas generation, and a reference electrode.

During a solution measurement cycle, the central electrode is detachably connected to the central measurement device for ORP measurements of the sample solution, as shown in FIG. 3A.

After the solution measurement cycle, the central electrode may become passivated due to solid or liquid residues formed thereon. In such a case, a cleaning cycle may start, in which the central electrode is disconnected or detached from the central measurement device, and both the central and the auxiliary electrodes are subsequently connected to the auxiliary current source (with an operating voltage of about 5–12 VAC) in a detachable manner, as shown in FIG. 3B. Electrical current passes through the central and auxiliary electrodes, generating gas bubbles and providing a vigorous surface process, which peels away solid or liquid residues on the electrode surface that may passivate the central electrode's response to the electropotential changes in the sample solution.

In such a way, the central electrode is cleaned and reactivated, and is ready to be reconnected to the central measurement device for the next solution measurement cycle.

The present invention has many potential applications in fluidic analysis, semiconductor process monitoring, and environmental controls. The examples provided hereinabove are not intended to limit the use of the present invention in any manner, and a person ordinarily skilled in the art can readily modify the present invention to meet the system requirements of a specific use.

Although the invention has been variously disclosed herein with reference to illustrative embodiments and features, it will be appreciated that the embodiments and features described hereinabove are not intended to limit the scope of the invention, and that other variations, modifications and other embodiments will suggest themselves to those of ordinary skill in the art. The invention therefore is to be broadly construed, consistent with the claims hereafter set forth.

What is claimed is:

1. An electrode assembly for collecting analytical signals from a sample solution, comprising:
   (a) a first electrode;
   (b) a measurement circuit;
   (c) an auxiliary electrode; and
   (d) an auxiliary current source,
      wherein said first electrode is detachably connected to said measurement circuit during a measurement and is not connected to the auxiliary current source, for collecting analytical signals from said sample solution, and wherein said first and auxiliary electrodes are detachably connected to said auxiliary current source during a cleaning and are not connected to the auxiliary current source to generate gas for in-line cleaning of said electrode assembly.

2. The electrode assembly of claim 1, wherein said first and auxiliary electrodes comprises one or more metals or metal alloys.

3. The electrode assembly of claim 1, wherein said first and auxiliary electrodes comprise platinum or platinum alloys.

4. The electrode assembly of claim 1, wherein during the cleaning period, said first and auxiliary electrodes are immersed in a conductive electrolytic solution.

5. The electrode assembly of claim 4, wherein said conductive electrolytic solution comprises an acid solution.

6. The electrode assembly of claim 1, wherein said first electrode is constructed and arranged to measure oxidation-reduction-potential.

7. The electrode assembly of claim 1, wherein the auxiliary current source is constructed and arranged for use solely to generate gas for said in-line cleaning.

8. The electrode assembly of claim 7, constructed and arranged for detachment of said first electrode and said auxiliary electrode from said measurement circuit after the measurement period, and attachment of said first electrode and said auxiliary electrode to said auxiliary current source for said in-line cleaning during said cleaning period.

9. The electrode assembly of claim 1, further comprising a reference electrode, wherein the reference electrode is constructed and arranged to be connected to the measurement circuit during said measurement period and during said cleaning period.

10. The electrode assembly of claim 9, constructed and arranged for detachment of said first electrode from said measurement circuit after the measurement period, and attachment of said first electrode and said auxiliary electrode to said auxiliary current source for said in-line cleaning during said cleaning period.

11. The electrode assembly of claim 10, wherein said auxiliary current source is constructed and arranged to provide an operating voltage of about 5–12 volts AC.

12. The electrode assembly of claim 1, constructed and arranged for conducting potentiometric titration of a reduction-oxidation species in said sample solution.

13. The electrode assembly of claim 1, constructed and arranged for measuring a characteristic oxidation-reduction-potential of said sample solution.

14. A method for rejuvenating a passivated measurement electrode, by providing an electrode assembly comprising (1) a measurement electrode, (2) a measurement circuit, (3) an auxiliary electrode, and (4) an auxiliary current source, wherein said measurement electrode is detachably connected to the measurement circuit during a measurement period for collecting analytical signals from a sample solution, and wherein said measurement electrode is passivated due to formation of solid and/or liquid residues thereon, said method comprising the steps of:

(a) disconnecting said measurement electrode from the measurement circuit; and (b) detachably connecting said measurement electrode and the auxiliary electrode to the auxiliary current source, so as to generate gas that removes the solid and/or liquid residues from the measurement electrode and rejuvenating said measurement electrode.

15. The method of claim 14, wherein said measurement and auxiliary electrodes comprises one or more metals or metal alloys.

16. The method of claim 14, wherein measurement and auxiliary electrodes comprise platinum or platinum alloys.

17. The method of claim 14, wherein said central and auxiliary electrodes are immersed in a conductive electrolytic solution in step (b).

18. The method of claim 17, wherein said conductive electrolytic solution comprises an acid solution.

19. The method of claim 14, wherein said measurement electrode is constructed and arranged to measure oxidation-reduction-potential.

20. An analytical cell including an electrode assembly arranged for automated self-cleaning, without disassembly and reassembly of the analytical cell, said analytical cell comprising:

a first electrode, an auxiliary electrode and optionally a reference electrode, as said electrode assembly;

a measurement circuit;

an auxiliary current source constructed and arranged for operation solely during said self-cleaning; and a sample solution in contact with said first electrode, said auxiliary electrode and, if present, said reference electrode;

wherein said first electrode, said auxiliary electrode and, if present, said reference electrode, are constructed and arranged:

(i) with the first electrode detachably connected to said measurement circuit during a measurement period, for collecting analytical signals from said sample solution;

(ii) with the first electrode and auxiliary electrode detachably connected to said auxiliary current source during a cleaning period, for said self-cleaning;

(iii) for detachment of said first electrode from said measurement circuit after the measurement period, and attachment of said first electrode and said auxiliary electrode to said auxiliary current source for said self-cleaning during said cleaning period;

(iv) with the reference electrode, if present, connected to said measurement circuit;

(v) with the measurement circuit operatively connected to the electrode assembly only during the measurement period; and (vi) with the auxiliary current source operatively connected to the electrode assembly only during the cleaning period.

\* \* \* \* \*